United States Patent [19]
Kassai

[11] Patent Number: 4,753,643
[45] Date of Patent: Jun. 28, 1988

[54] DISPOSABLE DIAPER

[75] Inventor: Kenzou Kassai, Osaka, Japan

[73] Assignee: Aprica Kassai kabushikikaisha, Osaka, Japan

[21] Appl. No.: 17,064

[22] Filed: Feb. 20, 1987

[30] Foreign Application Priority Data

| Feb. 28, 1986 | [JP] | Japan | 61-45078 |
| Apr. 4, 1986 | [JP] | Japan | 61-79014 |
| Jul. 3, 1986 | [JP] | Japan | 61-157544 |
| Jul. 21, 1986 | [JP] | Japan | 61-172353 |
| Jul. 21, 1986 | [JP] | Japan | 61-172354 |
| Aug. 22, 1986 | [JP] | Japan | 61-197780 |
| Nov. 26, 1986 | [JP] | Japan | 61-282781 |

[51] Int. Cl.⁴ .................................. A61F 13/16
[52] U.S. Cl. .................. 604/359; 604/385 R
[58] Field of Search ............ 604/359, 385.1, 385.2, 604/397, 358

[56] References Cited

U.S. PATENT DOCUMENTS

| 2,690,415 | 9/1954 | Shuler | 604/359 |
| 3,856,014 | 12/1974 | Yamauchi | 604/359 |
| 3,868,955 | 3/1975 | Steiger et·al. | 604/359 |
| 3,875,942 | 4/1975 | Roberts et al. | 604/359 |
| 4,597,761 | 7/1986 | Buell | 604/397 |

*Primary Examiner*—John D. Yasko
*Attorney, Agent, or Firm*—W. G. Fasse; D. H. Kane, Jr.

[57] ABSTRACT

A disposable diaper which comprises an inner member (1) to be in contact with the skin of a wearer, an outwardly directed outer member (3) and an absorbent member (4) interposed between the same, as well as elastic gathers (5) formed along portions close to both side edges (6) thereof. Baby powder (8) is retained in a pulverulent state in cavities (9) or wrinkles defined in the inner member by the gathers.

13 Claims, 11 Drawing Sheets

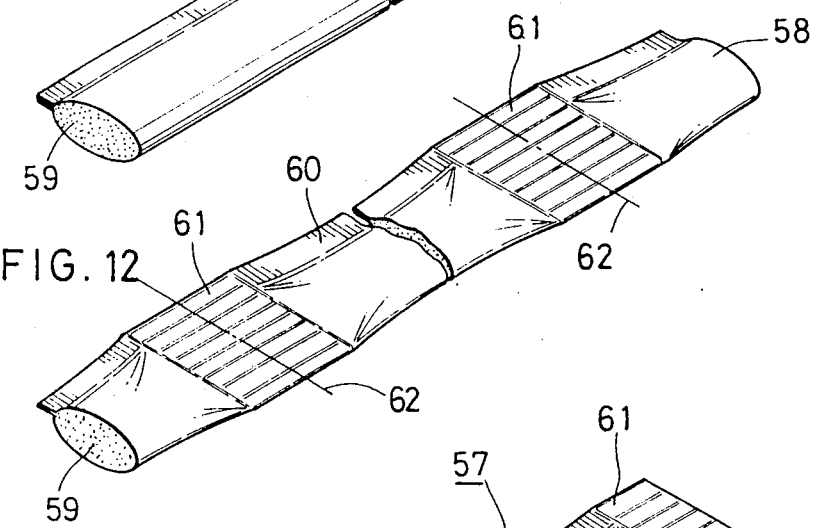
FIG. 11
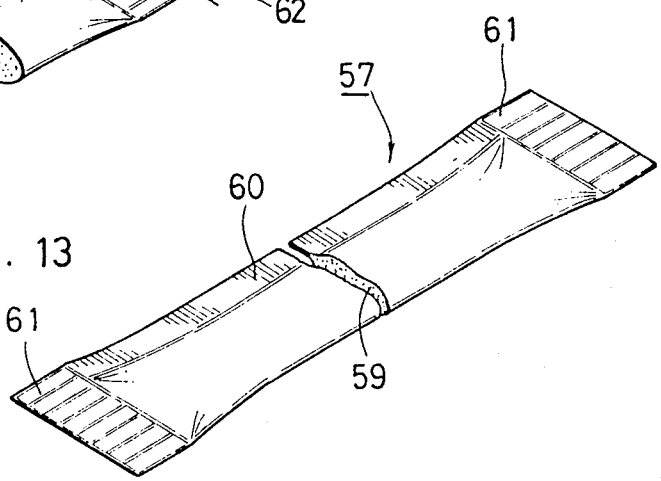
FIG. 12
FIG. 13

DISPOSABLE DIAPER

FIELD OF THE INVENTION

The present invention relates to a disposable diaper.

DESCRIPTION OF THE PRIOR ART

A disposable diaper generally has an inner member to be in contact with the skin of a baby or sick person, an outwardly directed outer member and an absorbent member interposed between the inner and outer members. The inner member is generally made of water-permeable nonwoven fabric, and the outer member is made of a waterproof film.

Such a convenient disposable diaper has come into wide use in recent years, and manufacturers of the disposable diaper have made various studies for improving the material and structure thereof to provide more handy products.

On the other hand, baby powder has been generally employed for changing the diaper, to protect the skin of the baby or sick person against prickly heat and sores. Further, a bad smell given out from egesta can be prevented by appropriate perfume contained in the baby powder.

However, such employment of the baby powder for changing the diaper is relatively troublesome since the baby powder must be always provided at hand and it takes time to change the diaper.

SUMMARY OF THE INVENTION

Accordingly, the present invention is directed to provide a disposable diaper which can effectively solve the aforementioned problem of the prior art.

Briefly stated, the present invention provides a disposable diaper which comprises an inner member to be in contact with the skin of a baby or sick person, an outwardly directed outer member and an absorbent member interposed between the inner and outer members. Baby powder is supplied in relation to the inner member, to be retained on the inner member in a pulverulent state.

According to the present invention, the baby powder can be applied by simply putting the disposable diaper on a baby or sick person. Namely, in the disposable diaper according to the present invention, the baby powder is retained in a pulverulent state in relation to the inner member to be in contact with the skin, whereby the baby powder is applied to the skin of the baby or sick person upon putting a new disposable diaper on him.

Therefore, it is not necessary to separately use the baby powder when changing the diaper, whereby the troublesome application of the baby powder for changing the diaper can be omitted to reduce the time for changing the diaper.

A preferred embodiment of the present invention is provided with means for improving the durability of retaining the baby powder on an inner member. For example, the inner member is formed by material allowing permeation of water as well as the baby powder, and the baby powder is sprinkled on the rear surface of the inner member in a pulverulent state or cavities are distributed in a plurality of portions of the inner member to receive the baby powder in a pulverulent state. The cavities may be positively formed by, e.g., embossing the inner member, or formed through wrinkles defined by gathers generally formed on both side edge portions of the disposable diaper. Further, in order to improve durability in retention of the baby powder, the baby powder may be received in bags provided with pores, which bags are to be added in the vicinity of both side edges of the diaper, or doubled portions being Z-shaped in section, for example, may be formed in the vicinity of the both side edge portions of the inner member to receive the baby powder in clearances defined in the doubled portions. Alternatively, elastic members may be provided by flexible foam material for forming elastic gathers in the diaper, whereby the baby powder can be placed in the bubbles or hollow spaces formed by the gathers.

Thus, retention durability for keeping the baby powder in place is so improved that the baby powder is gradually fed to the front side of the inner member, whereby the effect of the baby powder is excellently retained to effectively prevent prickly heat and sores. Further, a bad small can be prevented for a long time by employing baby powder containing perfume.

In another preferred embodiment of the present invention, baby powder is selectively supplied to portions close to both side edges of the inner member. Such portions close to the side edges are generally not directly moistened by urine of a baby or sick person, whereby the baby powder received therein can be maintained in a pulverulent state for a long time. Thus, the effect of the baby powder can be excellently maintained. Further, both side edge portions of the diaper are more frequently moved following movement of the baby or sick person as compared with other portions, whereby a large amount of baby powder can be fed to the front side of the inner member particularly if some means is provided to improve the retention durability for the baby powder as hereinabove described. In case of a diaper provided with elastic gathers in the vicinity of both side edges thereof, the gathers are extended the diaper is in use, whereby an impact caused by such extension is adapted to feed a larger amount of baby powder to the front side of the inner member. Thus, the effect of the baby powder can be expected from an initial stage of employment ot the disposable diaper.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 11 to 13 are perspective views showing exemplary manufacturing steps for obtaining a bag for receiving baby powder as employed in the embodiment of FIG. 10;

DESCRIPTION OF THE PREFERRED EMBODIMENTS

Figure 1:
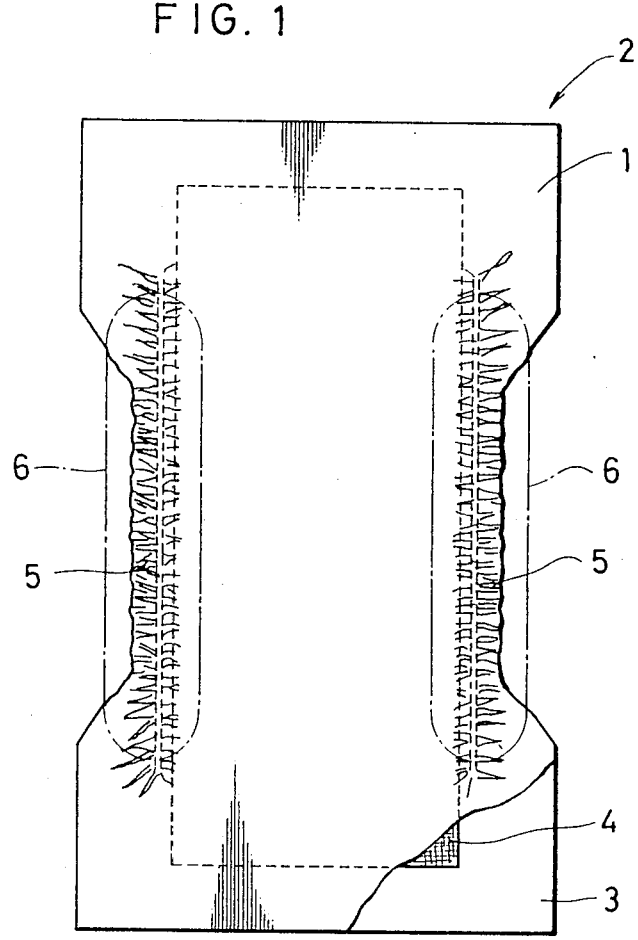
FIG. 1 is a plan view showing a disposable diaper according to an embodiment of the present invention.

FIG. 1 is a plan view showing a disposable diaper 2 according to an embodiment of the present invention with an inner member 1 being in an upwardly directed state. The inner member 1 is overlapped with an outer member 3 of a substantially identical configuration so that an absorbent member 4 is interposed between the inner and outer members. The absorbent member 4 is so positioned as to leave margins in the peripheral edge portions of the disposable diaper 2.

Elastic gathers 5 are preferably formed in at least a portion of each opposed side edge of the disposable diaper 2 which also has opposed end edges.

As to the material for forming each element of the disposable diaper 2, the inner member 1 is made water-permeable nonwoven fabric which is obtained by mixing polypropylene, polyethylene and pulp or polypropylene and polyester, and such mixture may contain calcium carbonate. The absorbent member 4 is mainly composed of flocculent pulp, which may contain a water absorptive high polymer. Both sides of the absorbent member 4 may be covered by cloth pulp members of, e.g., rayon cotton in order to retain the aforementioned flocculent pulp in shape. The outer member 3 is formed to be waterproof by a film of, e.g., low-density polyethylene, which film may be provided with a larger number of pores to attain gas permeability or calcium carbonate may be mixed therein in order to improve surface smoothness.

Figure 2:
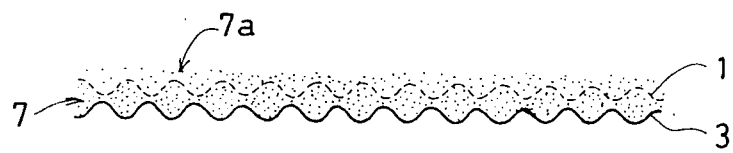
FIG. 2 is an enlarged sectional view illustrating one of side edge portions as shown in FIG. 1.

FIG. 2 is an enlarged sectional view illustrating one of both side edge portions 6 of the disposable diaper 2 as shown in FIG. 1. As seen from FIG. 2, baby powder 7 is sprinkled in a pulverulent state on the rear surface of the inner member 1 on the side edge portion 6 of the disposable diaper 2. As shown in FIG. 2, each of the side edge portions 6 of the disposable diaper 2 is a two-layer structure formed by the inner and outer members 1 and 3, whereby the baby powder 7 is held and retained between the inner and outer members 1 and 3.

The baby powder 7 may be sprinkled on the rear surface of either the inner member 1 or the outer member 3 in an intermediate step of manufacturing the disposable diaper 2 before overlapping the inner and outer members 1 and 3.

As shown in FIG. 2, the baby powder 7 received on the rear surface of the inner member 1 of, e.g., nonwoven fabric, gradually passes through the inner member 1, so that baby powder 7a thus passing through the inner member 1 directly acts on the skin of a baby or sick person. Being selectively sprinkled on the both side edge portions 6 of the disposable diaper 2 as shown in the figure, the baby powder 7 can be maintained in the pulverulent state since the side edge portions 6 are not directly moistened by urine of the baby or sick person in general. Thus, the effect of the baby powder 7 can be persistently maintained. In response to movement by the wearer, the side edge portions 6 are more frequently moved as compared with other portions, whereby a larger amount of the baby powder 7 can be fed to the front surface of the inner member 1. Further, the gathers 5 are extended when the disposable diaper 2 is in use, whereby the baby powder 7 is further fed to the front surface of the inner member 1 by forces caused by such extension. Thus, the effect of the baby powder 7a can be expected from an initial stage of employment of the disposable diaper 2, while fragrance given out from the baby powder 7a effectively suppresses a bad small given out in change of the diaper.

Although the regions to be supplied with the baby powder 7 may be restricted to both side edge portions 6 of the disposable diaper 2 in the aforementioned embodiment, the baby powder 7 may be sprinkled substantially over the entire diaper 2.

In the aforementioned embodiment, the baby powder 7 is applied to the rear surface of the inner member 1 in the stage of manufacturing the disposable diaper in order to securely retain the baby powder 7 thus applied in relation to the inner member 1, while means for securely retaining the baby powder 7 can be modified in various manners, as hereinafter described.

Figure 3:
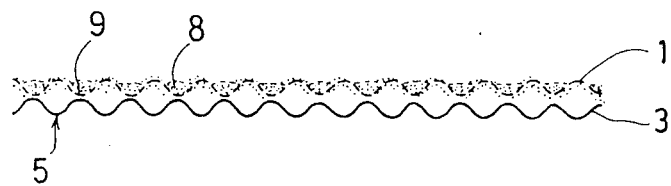
FIG. 3 is a sectional view corresponding to FIG. 2, showing another embodiment of the present invention.

FIG. 3 is a view corresponding to FIG. 2, showing another exemplary mode of retaining baby powder. Referring to FIG. 3, portions corresponding to those in FIGS. 1 and 2 are indicated by the same reference numerals.

Referring to FIG. 3, inner and outer members 1 and 3 are wrinkled by gathers 5 formed in both side edge portions 6 (see FIG. 1) of a disposable diaper. As the result of such wrinkling, a plurality of cavities 9 are defined in the inner member 1. Such cavities 9 are adapted to receive baby powder 8 in a pulverulent state. The baby powder 8 is sprinkled on the region provided with the cavities 9, to be introduced into the cavities 9 by a brush, for example.

The baby powder 8 may be any commercially available powder suitable for the intended purpose. For example, "Baby Powder" by Johnson & Johnson can be effectively embedded in the cavities 9, with fragrance being given out in the circumference.

Figure 4:
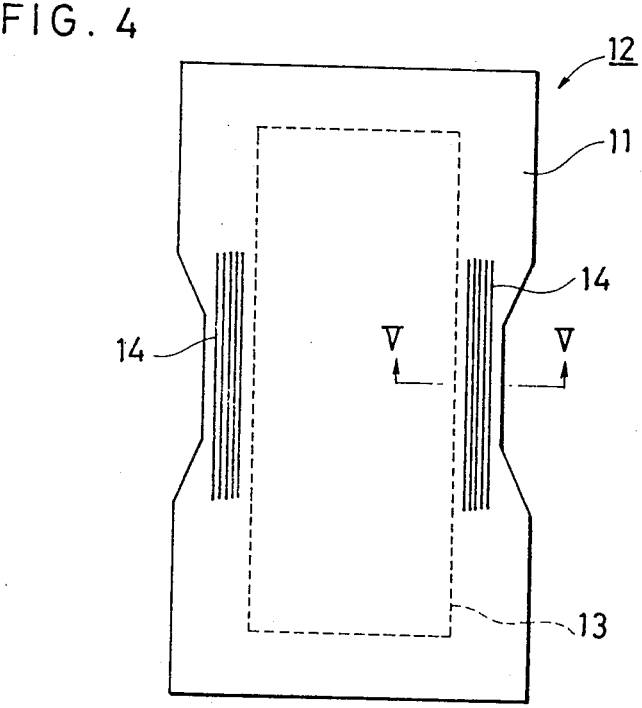
FIG. 4 is a plan view showing a disposable diaper according to still another embodiment of the present invention.

FIG. 4 is a plan view showing a disposable diaper 12 according to still another embodiment of the present invention, with an inner member 11 being in an upwardly directed state. An absorbent member 13 is positioned under the inner member 11, as shown by dotted lines.

As seen from FIG. 4, a plurality of cavities 14 are formed by grooves distributed in the vicinity of both side edges of the inner member 11. Particularly in this embodiment, the cavities 14 are concentrated in portions to be in contact with the thigh of a baby or sick person.

Figure 5:
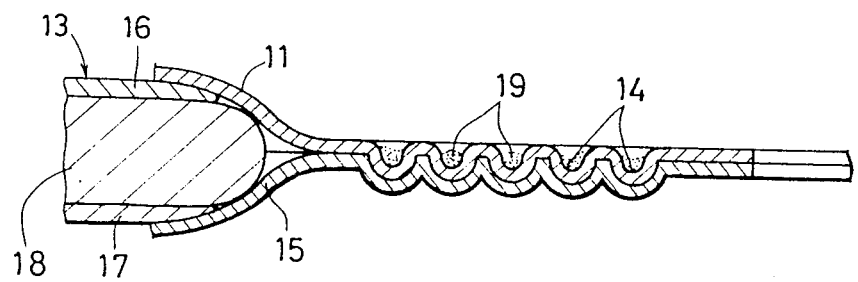
FIG. 5 is an enlarged sectional view taken along the line V—V in FIG. 4.

FIG. 5 is an enlarged sectional view taken along the line V—V in FIG. 4. An outer member 15 is adhered with the aforementioned inner member 11. An absorbent member 13 is constructed as a three-layer structure, with a flocculent member 18 being interposed between two cloth members 16 and 17.

As obviously shown in FIG. 5, the aforementioned cavities 14 are formed in the portions of the inner member 11 adhered with the outer member 15. Such cavities 14 can be readily formed in a cutting stage performed in the steps of manufacturing the disposable diaper 12. Namely, a die for cutting can be provided with shapes for forming the cavities 14, so that the cavities 14 can be formed by the so-called embossing. In order to assure the formation of the cavities 14, the embossing may be performed under application of heat. The cavities 14 may be formed in a stage separate from the cutting stage.

A plurality of such groove-shaped cavities 14 are formed on each side edge of the inner member 14 preferably at intervals of about 1 mm.

As shown in FIG. 5, the cavities 14 are adapted to receive baby powder 19 in a pulverulent state.

Figure 6:
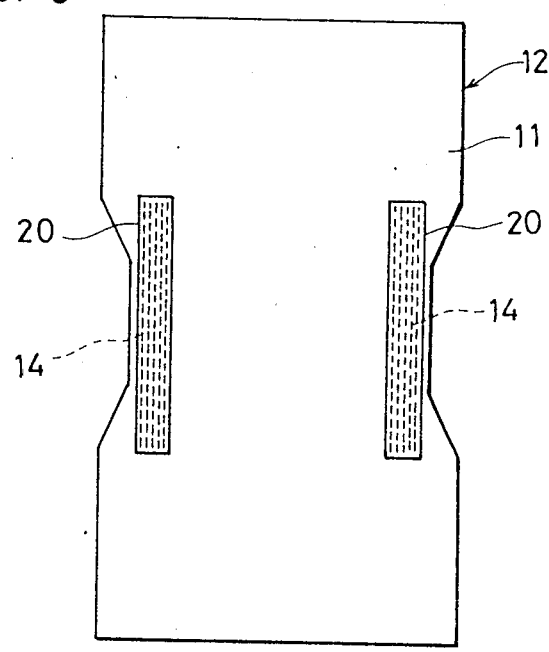
FIG. 6 is a plan view showing a disposable diaper according to a further embodiment of the present invention.

FIG. 6 shows a further embodiment of the present invention, in which tapes 20 are added to the disposable diaper 12 as shown in FIG. 4. The tapes 20 are provided with large numbers of pores to be water-permeable, and are adhered to the inner member 11 to cover the aforementioned cavities 14.

According to the embodiment of FIG. 6, baby powder 19 is further durably retained in the cavities 14 to be further effectively prevented from being scattered prior to using the disposable diaper 12, while the effective state of the baby powder 19 can be further maintained after employment of the disposable diaper 12.

The aforementioned tapes 20 may be elastic particularly in the longitudinal direction. When such elastic tapes 20 are adhered to the inner member 11 in extended states, elastic fit gathers are naturally defined along both side edges of the disposable diaper 12 by shrinkage of the tapes 20 themselves.

Further, the tapes 20 may be made of material shrinkable upon absorption of water, so that the tapes 20 are shrunk in response to lateral leakage of urine, to prevent such lateral leakage on both side edges of the disposable diaper 12.

Figure 7:
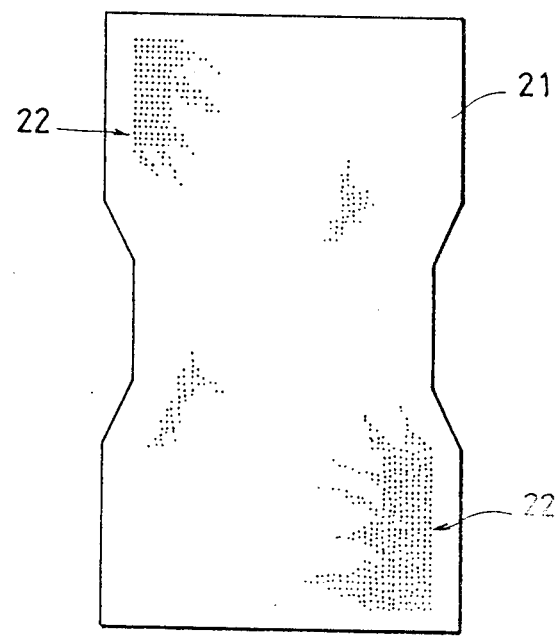
FIG. 7 is a plan view showing an inner member employed in a further embodiment of the present invention.

FIG. 7 shows a further embodiment of the present invention, in which cavities 22 are distributed substantially over the entire surface of an inner member 21, in the form of dots.

The cavities 22 in the form of dots can effectively retain baby powder therein similarly to the aforementioned groove-shaped cavities 14 (see FIG. 5). When such cavities 22 are distributed substantially over the entire surface of the inner member 21, the effect of the baby powder can be applied to in a wider range.

When the cavities 22 are thus formed substantially over the entire surface of the inner member 21, the same are preferably formed before the inner member 21 is assembled with other elements of the disposable diaper.

The dot-shaped cavities 22 as shown in FIG. 7 may be distributed only in the vicinity of the both side edges of the inner member 21 similarly to the groove-shaped cavities 14 as shown in FIG. 4. On the other hand, the groove-shaped cavities 14 as shown in FIG. 4 may be distributed substantially over the entire surface of the inner member 21.

Figure 8:
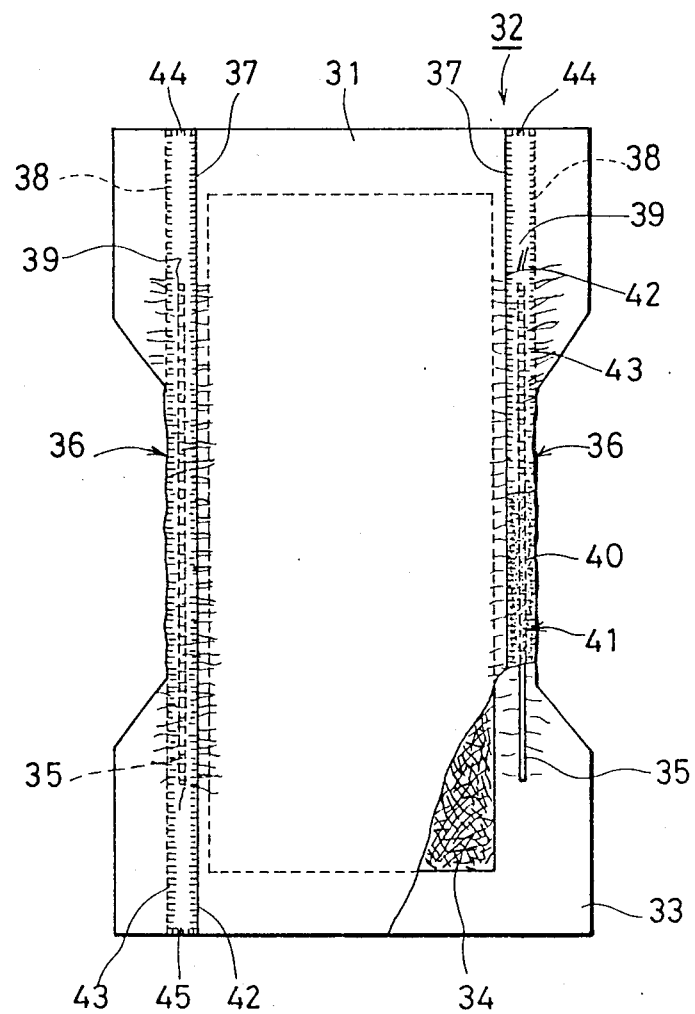
FIG. 8 is a plan view showing a disposable diaper according to a further embodiment of the present invention, with an inner member being illustrated in a partially fragmented manner.

FIG. 8 is a plan view showing a disposable diaper 32 according to a further embodiment of the present invention, by an inner member 31 being in an upwardly directed state. The inner member 31 is overlapped with an outer member 33 having a substantially identical configuration, so that an absorbent member 34 is interposed between the inner and outer member.

Longitudinal elastic members 35 are provided on both side edges of the disposable diaper 32 between the inner and outer members 31 and 33, thereby to form elastic gathers 36.

Figure 9:
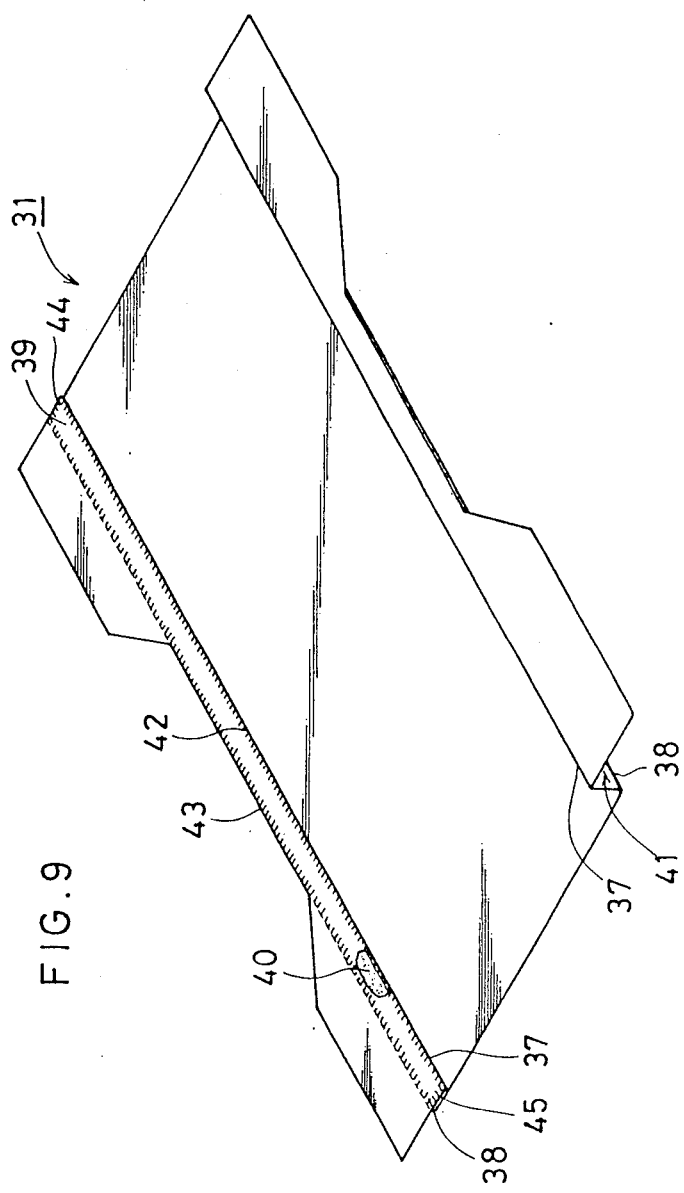
FIG. 9 is a perspective view independently showing the inner member of FIG. 8, which is in the middle stage of the manufacturing steps.

FIG. 9 is a perspective view of the inner member 31 as shown in FIG. 8. FIG. 9 shows an intermediate stage of manufacturing the inner member 31, in order to facilitate understanding of its structure.

A doubled portion 39 having a Z-shaped section and being provided with a pair of oppositely bent parallel folds 37 and 38 is formed in the vicinity of each side edge of the inner member 31, to extend longitudinally along the side edge. FIG. 9 shows the doubled portion 39 on the other side in a partially fragmented manner, which doubled portion 39 is filled with baby powder 40. As to the side edge shown on this side of FIG. 9, such baby powder 40 is received in a clearance 41 defined in the inner side of a portion bent along the fold 37.

In order to prevent the baby powder 40 from being scattered through the clearance 41, opening portions of the clearance 41 are closed. As shown on the opposite side edge of FIG. 9, the fold 37 is joined with a flat surface part of the inner member 31 overlapped therewith in a joint portion 42 while the fold 38 is joined with another flat surface part of the inner member 31 overlapped therewith in a joint portion 43. More preferably, joint portions 44 and 45 are formed on both end portions of the fold 38. Thus, a closed bag-like member is defined in the portion bent through the fold 37, thereby to substantially prevent the baby powder 40 from being scattered through the clearance 41.

Since the nonwoven fabric forming the inner member 31 contains thermoplastic resin as hereinabove described, the joint portions 42 to 45 are preferably formed by fusion welding. In place of such fusion welding, an adhesive agent or the like may be applied.

The inner member 31 formed as shown in FIG. 9 is joined with the outer member 33 by, e.g., fusion welding in a state sandwiching the absorbent member 34 and the elastic members 35, as shown in FIG. 8. The diaper 32 thus obtained retains the baby powder 40 on the rear side of the inner member 31 in the vicinity of both side edges thereof. The baby powder 40 passes through the inner member 31 to reach the front side of the inner member 31, thereby to directly act on the skin of a baby or sick person.

Although the doubled portions 39 defining the clearances 41 for receiving the baby powder 40 are bent along the folds 37 located on the sides to be directly in contact with the skin in the aforementioned embodiment, the baby powder 40 may be filled in clearances defined in the inner sides of the portions bent along the folds 38 while the same may be received in both clearances.

Further, although the upper surface of the inner member 31 as shown in FIG. 9 is upwardly directed to be in contact with the skin in the disposable diaper 32 as shown in FIG. 8, the lower side of FIG. 9 may be upwardly directed to be in contact with the skin.

As shown in FIG. 9, the doubled portions 39 do not define any large step with respect to other portions of the inner member 31 upon formation of the joint portions 42 along the folds 37 to make the diaper more comfortable to its wearer. However, if such an advantage is not desired, the folds 37 may not necessarily be joined with the flat surface parts of the inner member 31.

When, to the contrary, the baby powder 40 is to be received not in the illustrated portions but in the clearances defined in the inner sides of the folds 38, the folds 38 may not be joined with the flat surface parts of the inner member 31 by the joint portions 43.

Although the baby powder 40 is sprinkled substantially entirely over the longitudinal doubled portions 39, the same may be concentrated substantially to longitudinal central regions of the doubled portions 39.

Although the joint portions 43 are formed to prevent the baby powder 40 from being scattered through the clearances 41 as shown in FIG. 9, the baby powder 40 may not be completely prevented from being scattered in such joint portions, but clearances may be formed to allow slight scattering of the baby powder 40.

Figure 10:
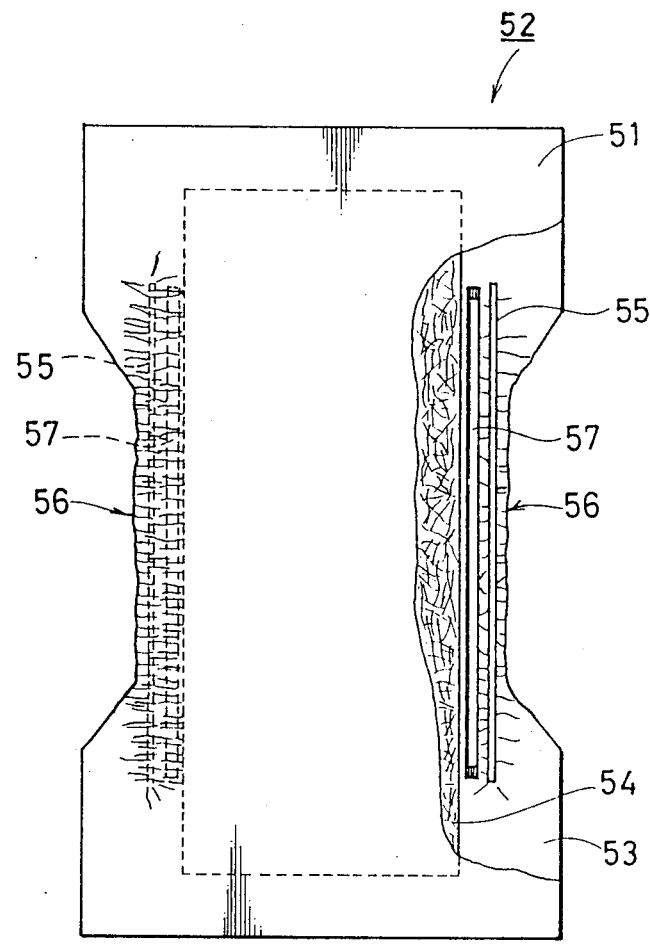
FIG. 10 is a plan view showing a disposable diaper according to a further embodiment of the present invention, with an inner member being illustrated in a partially fragmented manner.

FIG. 10 is a partially fragmented plan view showing a disposable diaper 52 according to a further embodiment of the present invention, with an inner member 51 being in an upwardly directed state. The inner member 51 is overlapped by an outer member 53 having a substantially identical configuration, so that an absorbent member 54 is interposed between the inner and outer member.

Longitudinal elastic members 55 are provided in the vicinity of both side edges of the disposable diaper 52, thereby to form elastic gathers 56.

Referring to FIG. 10, longitudinal cylindrical bags 57 are arranged between the elastic members 55 for forming the gathers 56 and respective side edges of the absorbent member 54. These bags 57 are adapted to receive baby powder in a pulverulent state. An exemplary method of manufacturing such a bag 57 will now be described with reference to FIGS. 11 to 13.

As shown in FIG. 11, a strip-shaped sheet 58 having a large number of pores is first prepared, e.g. of a sheet of nonwoven fabric identical to the material for the inner member 51 or of relatively porous paper. Then the sheet is cylindrically rounded to for a cylinder type member for receiving baby powder 59 in the the cylinder type member. Both opening edges 60 of the sheet 58 are joined with each other by fusion welding or adhesion, for example. The opening edges 60 may have been previously joined to each other so that the sheet 58 is approximately cylindrically formed to receive the baby powder 59.

Then, as shown in FIG. 12, upper and lower portions of the cylindrical sheet 58 are joined to each other at appropriate intervals through, e.g., fusion welding, so that a plurality of sealing portions 61 are distributed in the longitudinal direction. One of adjacent sealing portions 61 may have been previously formed to receive a prescribed amount of the baby powder 59 in the cylindrical sheet 58, to thereafter form the other sealing portion 61.

The structure as shown in FIG. 12 is wound around, e.g., a reel (not shown), to be cut along cutting lines 62 on the production line, so that the bag 57 of prescribed length as shown in FIG. 13 is interposed between the inner and outer members 51 and 53 as shown in FIG. 10

Then the bag 57 is fusion-welded or adhered to the inner member 51 and/or the outer member 53, the inner and outer members 51 and 53 are fusion-welded or adhered to each other in the circumference of the bag 57, or both of such operations are performed, thereby to locate the bag 57 in a prescribed position on the diaper 52.

When such a disposable diaper 52 is in use, the baby powder 59 received in the bags 57 passes through the pores formed in the same to reach the outer sides of the bags 57 and pass the water-permeable inner member 51 of nonwoven fabric or the like, thereby to be in contact with the skin of the wearer.

As in the aforementioned embodiment, the bags 57 for receiving the baby powder 59 may be manufactured by a number of continuous steps, whereby excellent productivity can be expected.

The bags 57 featuring this embodiment can be obtained through other manufacturing methods, and the entire configuration thereof is not restricted to the longitudinal one. For example, a plurality of relatively short bags may be arranged in the vicinity of each edge of the diaper.

Although the bags 57 are provided on the inner sides of the elastic members 55 for forming the gathers 56 so that they will not obstruct the formation of the gathers 56 by shrinkage of the elastic members 55 in this embodiment, positions of arrangement of such bags 57 can be arbitrarily selected if the aforementioned advantage is not desired.

Further, although the bags 57 are arranged between the inner and outer members 51 and 53, i.e., on the rear side of the inner member 51 in this embodiment, the same may be arranged on the front side of the inner member 51, for example.

Figure 14:
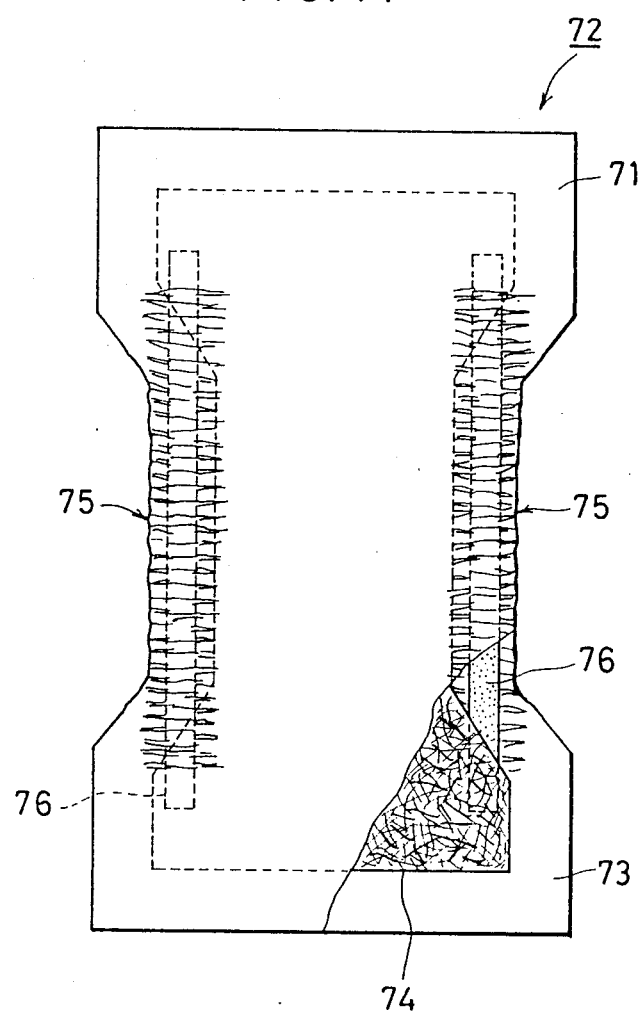
FIG. 14 is a plan view showing a disposable diaper according to a further embodiment of the present invention, with an inner member being illustrated in a partially fragmented manner.

FIG. 14 is a plan view showing a disposable diaper 72 according to a further embodiment of the present invention, with an inner member 71 being in an upwardly directed state. The inner member 71 is overlapped with an outer member 73 having a substantially identical configuration, so that an absorbent member 74 is interposed between the same.

The inner and outer members 71 and 73 respectively are made of thermoplastic resin, and fusion welding is applied to, e.g., the peripheral edge portion in manufacturing of the diaper 72 since the inner and outer members 71 and 73 are integrated in a combined state with each other. Joint portions may be also distributed in a plurality of positions between the inner member 71 and/or the outer member 73 and the absorbent member 74. In such joint portions, an adhesive agent may be employed in addition to the fusion welding.

As shown in FIG. 14, elastic gathers 75 are provided in the vicinity of both side edges of the diaper 72. Longitudinal elastic members 76 are employed to form such gathers 75. The elastic members 76 are preferably made of relatively wide tape-like members of 13 mm in width and 2.0 mm in thickness, for example. In order to form the gathers 75, both end portions of the elastic members 76 are fixed to, e.g., the outer member 73 in extended states. The elastic members 76 may be joined with the inner member 71 and/or the outer member 73 in a plurality of portions of longitudinal centers thereof, if necessary.

Figure 15:
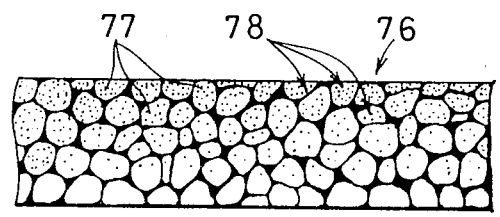
FIG. 15 is an enlarged sectional view of an elastic member as shown in FIG. 14.

FIG. 15 is an enlarged sectional view of such an elastic member 76. The elastic member 76 is made of flexible foam material such as polyurethane foam material. The elastic member 76 of such flexible foam material has an elasticity in its longitudinal direction as well as in the direction of thickness, to provide soft touch through the inner member 71.

A plurality of bubbles 77 or hollow spaces are formed in the elastic member 76 of flexible foam material, to receive baby powder 78 in a pulverulent state. Particularly in this embodiment, the baby powder 78 is different in density of distribution in the direction of thickness of the elastic member 76, as shown in FIG. 15.

Namely, the baby powder 78 is distributed in larger amounts in the bubbles 77 opening in the upwardly directed surface of the elastic member 76 as shown in FIG. 15, i.e., the surface facing the inner member 71. Such a state of distribution is so selected that the baby powder 78 can be further efficiently fed to the front side of the inner member 71, for reducing the amount of the baby powder that cannot act to the last in employing of the diaper 72.

In order to obtain the aforementioned state of distribution of the baby powder 78, the baby powder 78 may be sprayed toward the upper surface of the elastic member 76 as shown in FIG. 15, for example. In response to this, the amount of the baby powder 78 received in the upwardly opening bubbles 77 is naturally increased. While the foam material forming the elastic members 76 includes a closed cell type, an open cell type or an intermediate type, the baby powder 78 can be received in the bubbles 77 located in the intermediate portion of the elastic member 76 in the direction of thickness, so far as the foam material is not completely of the closed cell type. The baby powder 78 may be applied to the elastic member 76 by applying a vacuum to the elastic member 76 from the lower side and sprinkling the baby powder 78 on the upper surface thereby to introduce the baby powder 78 into the bubbles 77 as shown in FIG. 15, so far as the elastic member 76 is not completely of the close cell type foam material.

In the steps of manufacturing the disposable diaper 72, the step of supplying the baby powder 78 to the elastic member 76 is preferably performed as late as possible, so that the baby powder 78 thus supplied is not scattered in subsequent steps.

Although the elastic members 76 are in a tape-like configuration in this embodiment, the same may be in a string-shaped configuration, while a plurality of such elastic members may be used for each side edge of the diaper 72.

In each of the aforementioned embodiments as shown in FIGS. 1 and 2, FIG. 3, FIGS. 4 and 5, FIG. 6, FIG. 7 and FIGS. 8 and 9, technique is required to supply baby powder to prescribed positions of a disposable diaper. Description is now made of examples of a method and an apparatus for efficiently supplying the baby powder. The following method and apparatus for supplying baby powder are particularly suitable for supplying the baby powder in the vicinity of both side edges of a disposable diaper, as in the embodiment shown in FIG. 3.

Figure 16:
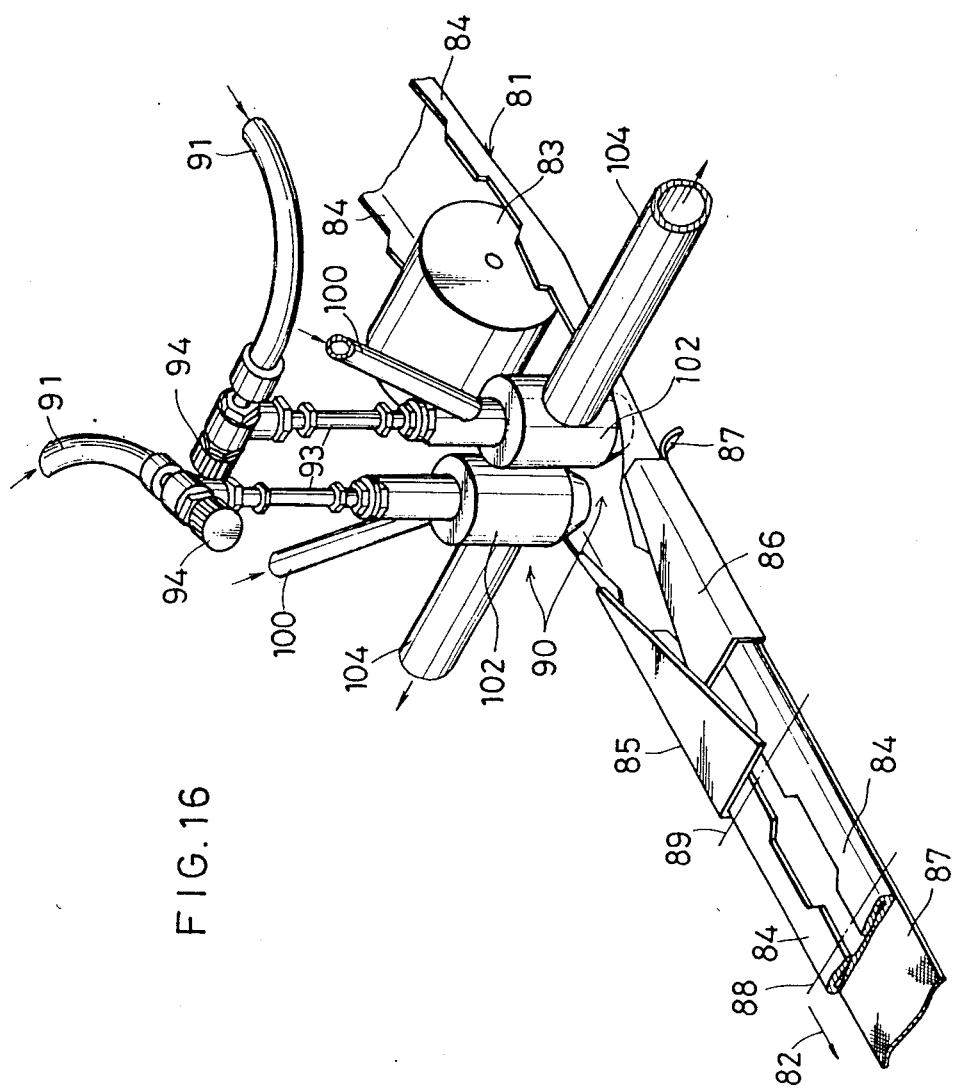
FIG. 16 is a perspective view showing principal parts of a baby powder supply device for use in the manufacture of disposable diapers according to the present invention.

As partially shown in FIG. 16, a disposable diaper is in the form of a laminated continuous sheet 81 obtained by laminating an inner member, an absorbent member and an outer member in an intermediate stage of manufacturing. The laminated continuous sheet 81 is fed in the direction as shown by an arrow 82, to be sequentially subjected to various working steps for manufacturing the disposable diaper. The stage as shown in FIG. 16 substantially corresponds to the final stage of such manufacturing steps, in which both side edges of the laminated continuous sheet 81 are inwardly bent prior to cutting.

As shown in FIG. 16, the upper surface of the laminated continuous sheet 81 is in pressure contact with a rotary drum 83 whose axial length is shorter than its width, so that both side edges 84 of the laminated continuous sheet 81 are slightly bent inwardly. Thereafter the laminated continuous sheet 81 is guided to a pair of opposite bending guide members 85 and 86. The bending guide members 85 and 86 are L-shapd or U-shaped in section, and the laminated continuous sheet 81 is held by a conveyor belt 87 introduced from the lower side and forcibly fed to pass through the bending guide members 85 and 86. As the laminated continuous sheet 81 is passing through the bending guide members 85 and 86, both side edges 84 are completely bent inwardly.

The laminated continuous sheet 81 thus completely bent is cut in positions 88 and 89 as shown by one-dot chain lines in FIG. 16, to form individual disposable diapers (not shown).

Figure 17:
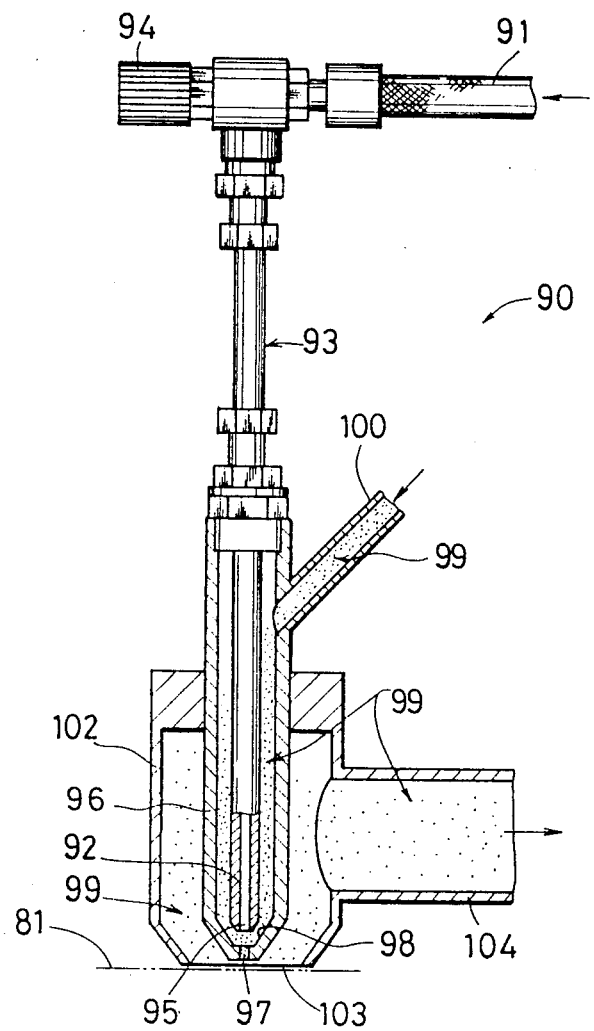
FIG. 17 is a partially fragmented front elevational view of one of the baby powder suppliers 90 as shown in FIG. 16.

Baby powder supply devices 90 according to this embodiment of the present invention are provided between the rotary drum 83 and the bending guide members 85 and 86. The baby powder supply devices 90 are provided in relation to respective ones of the side edge portions 84 of the laminated continuous sheet 81. FIG. 17 is a partially fragmented front elevational view showing one of the baby powder suppliers 90.

Referring to FIGS. 16 and 17, a compressed air source (not shown) for supplying compressed air of, e.g., about 3 to 4 kg/m$^2$ is coupled with compressed air introducing hoses 91, whereby the compressed air is introduced through the hoses 91 into conduits 93 having air nozzles 92 in end portions thereof. Pressure regulator handles 94 are provided in the coupling portions between the conduits 93 and the hoses 91, to regulate the pressure of the compressed air supplied to the air nozzles 92. Exhaust nozzles 95 are provided in the end portions of the air nozzles 92, to inject the compressed air.

A tubular temporary reservoir 96 is provided to encircle each of the air nozzles 92. The temporary reservoir 96 has an outlet 97 in a position being in contact with the compressed air injected from the exhaust nozzle 95, and a tapered inner peripheral surface 98 is formed in the end portion provided with the outlet 97. According to this embodiment, the exhaust nozzle 95 is coaxially located inside the outlet 97.

A conduit 100 for introducing baby powder 99 into the temporary reservoir 96 is provided in an upper part of the temporary reservoir 96. The conduit 100 is coupled to a baby powder feeder 101, as hereinafter described with reference to FIG. 18.

The air nozzle 92 is further provided with a cylindrical suction chamber 102, which encircles the tubular temporary reservoir 96. The suction chamber 102 has an opening 103 in an end surface facing the laminated continuous sheet 81. A sidewardly extending exhaust pipe 104 communicates with the space defined in the suction chamber 102. The exhaust pipe 104 is coupled with a vacuum pump (not shown) or the like, so that negative pressure is maintained to the suction chamber 102.

As obvious from FIG. 17, the end portion of the temporary reservoir 96 forming the outlet 97 is preferably located on substantially the same plane with the end surface of the suction chamber 102 forming the opening 103 or slightly inside thereof. Such location is so selected as to prevent the sharper end portion of the temporary reservoir 96 from being in direct contact with the upwardly directed surface of the laminated continuous sheet 81 of soft material to scratch the same. Since the end surface of the suction chamber 102 provided with the opening 103 has a relatively wide surface, the same may be in contact with the upwardly directed surface of the laminated continuous sheet 81 or define a small space therebetween.

Figure 18:
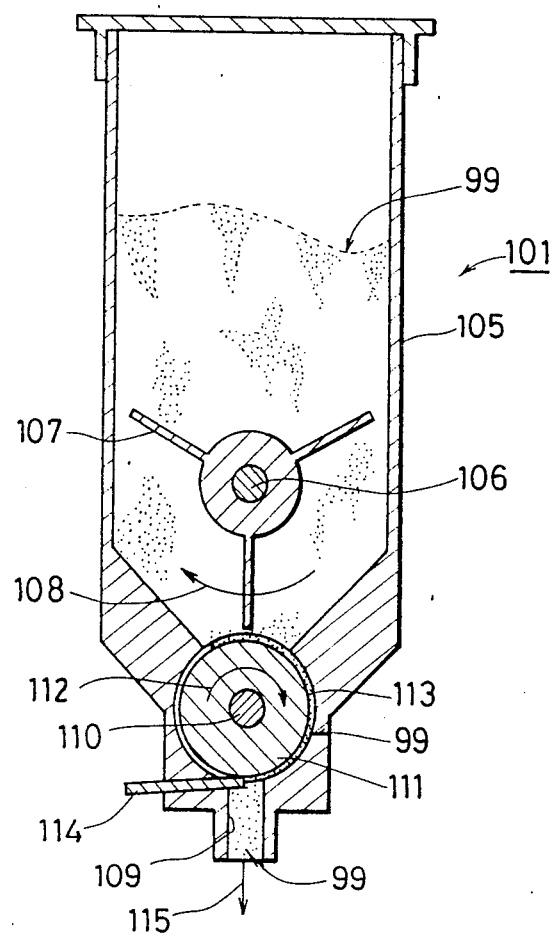
FIG. 18 is a sectional view showing an example of a baby powder feeder formed as a part of the baby powder supplier.

With reference to FIG. 18, the baby powder feeder 101 for feeding the baby powder 99 to the temporary reservoir 96 in a prescribed amount per unit time will now be described. This baby powder feeder 101 comprises a hopper part 105 for receiving and storing the baby powder 99. The hopper part 105 is provided with a stirring blade 107 having a rotary shaft 106 directed in, e.g., the horizontal direction. The stirring blade 107 is rotated in, e.g., a direction indicated by an arrow 108, thereby to prevent aggregation of the baby powder 99 stored in the hopper part 105. A discharge path 109 is formed in the lower end portion of the hopper part 105.

In the middle of the discharge path 109, a feed rotor 111 rotated by a rotary shaft 110 directed in, e.g., the horizontal direction is provided to close the discharge path 109. The feed rotor 111 is in contact with a wall plane defining the discharge path 109, to be rotated in, e.g., a direction shown by an arrow 112. The feed rotor 111 is provided with a circumferentially extending groove 113 having prescribed width. Thus, the groove 113 receives a prescribed amount of the baby powder 99. The baby powder 99 thus filled in the groove 113 passes through the discharge path 109 by rotation of the feed rotor 111, to reach a downwardly opening portion of the discharge path 109. A scraping member 114 is provided in the portion to project into the groove 113. The scraping member 114 scrapes the baby powder 99 filled in the groove 113 to downwardly drop the same. The baby powder 99 thus discharged from the discharge path 109 is fed into the temporary reservoir 96 through the conduit 100 as shown in FIGS. 16 and 17.

With reference to FIGS. 16 to 18, the operation of each baby powder supply devices 90 will now be described.

First, the compressed air is injected from the air nozzle 92 through the compressed air introducing hose 91 and the conduit 93. At this time, the injection force for the compressed air may be appropriately regulated by the pressure regulator handle 94.

On the other hand, the baby powder 99 is introduced into the hopper part 105 of the baby powder feeder 101 as shown in FIG. 18, and the stirring blade 107 and the feed rotor 111 are driven respectively. In response to this, the baby powder 99 filled in the groove 113 of the feed rotor 111 is fed to the outlet of the discharge path 109 with rotation of the feed rotor 111, to be downwardly dropped by the scraping member 114 as shown by an arrow 115, and then supplied to the temporary reservoir 96 through the conduit 100 as shown in FIGS. 16 and 17. In order to adjust the amount of the baby powder 99 supplied to the temporary reservoir 96, the r.p.m. of the feed rotor 111 may be appropriately adjusted, for example.

The baby powder 99 thus supplied to the temporary reservoir 96 reaches the tapered inner peripheral surface 98, to be in contact with the air injected from the exhaust nozzle 95 of the air nozzle 92. Thus, the baby powder 99 is injected onto one surface of the laminated continuous sheet 81 by the compressed air injected from the exhaust nozzle 95.

The positional relation between the pair of baby powder supply devices 90 and the laminated continuous sheet 81 as shown in FIG. 16, makes it clear that the baby powder 99 injected in the aforementioned manner is supplied in the vicinity of both side edge portions 84 of the laminated continuous sheet 81. The one surface of the laminated continuous sheet 81 thus supplied with the baby powder 99 corresponds to the front surface of the inner member of the disposable diaper, although not shown in detail in FIG. 16. Therefore, regions supplied with the baby powder 99 are formed along both side edges of the inner member in each of the disposable diapers obtained by cutting the laminated continuous sheet 81.

The laminated continuous sheet 81 thus supplied with the baby powder 99 immediately passes through the bending guide members 85 and 86, so that both side edges 84 thereof are completely bent with the surface supplied with the baby powder 99 being inwardly directed. Then, the laminated continuous sheet 81 is cut along the one-dot chain lines 88 and 89 as hereinabove described, to obtain individual disposable diapers.

As shown in FIG. 17, the end surface of the suction chamber 102 provided with the opening 103, defines a small clearance facing the upwardly directed surface of the laminated continuous sheet 81. Reduced pressure is applied to the clearance is through the exhaust pipe 104, whereby the baby powder 99 left therein without being in contact with the laminated continuous sheet 81, is removed by vacuum suction.

The location of the baby powder supplier 90 or the stage of supplying the baby powder 99 in the steps of manufacturing the disposable diaper may not be immediately in front of the passage through the bending guide members 85 and 86, i.e., immediately in front of the step of bending the both side edge portions of the laminated continuous sheet 81 as in the shown embodiment, but may be provided in advance to the same. Further, the air nozzle and the temporary reservoir may be modified in configuration, so that the baby powder 99 is injected through a clearance between the bent portions of the laminated continuous sheet 81.

The term "laminated continuous sheet being cut to form individual disposable diapers" in this specification may not include all of the elements for the disposable diapers. For example, a continuous sheet corresponding to inner members may not yet be laminated. Therefore, the baby powder may be supplied onto the absorbent members located under the inner members, thereafter to laminate the inner members. In relation to this, the laminated continuous sheet is called as "laminated continuous sheet being cut to form individual disposable diapers" even if the elastic members generally provided in disposable diapers for forming elastic gathers, fasteners for putting the diapers on babies and the like are not yet added.

The positional relation between the air nozzle 92 and the temporary reservoir 96 is not restricted to that in the shown embodiment. Namely, the temporary reservoir may be simply provided with the outlet in a position in contact with the compressed air injected from the exhaust nozzle of the air nozzle.

While the end portion of the temporary reservoir 96 forming the outlet 97 is effectively positioned on the same plane with the end surface of the suction chamber 102 having the opening 103 or slightly inside thereof not to obstruct smooth feeding of the laminated continuous sheet 81 and to facilitate effective operation of the negative pressure in the suction chamber 102, the end portion of the temporary reservoir 96 may project from the end surface of the suction chamber 102 if the said advantages are not desired.

Although the present invention has been described and illustrated in detail, it is clearly understood that the same is by way of illustration and example only and is not to be taken by way of limitation, the scope of the present invention being limited only by the terms of the appended claims.

What is claimed is:

1. A disposable diaper having opposed end edges and opposed side edges, comprising a water-permeable inner member for contacting the skin of a wearer; an outwardly directed waterproof outer member; water absorbent means interposed between said inner and outer members for absorbing body fluids; said water-permeable inner member comprising; first cavities distributed in a plurality of portions of said inner member so that said first cavities face the skin of a wearer; said diaper further comprising elastic gathers in at least a portion of each of said opposed side edges; said elastic gathers having wrinkles forming second cavities facing the skin of a wearer; and baby powder retained in a pulverulent state in said first and second cavities, whereby said first and second cavities provide an improved retention durability for said baby powder and assure a prolonged release of said baby powder with said disposable diaper is in use.

2. The disposable diaper of claim 1, wherein said first cavities are distributed in the vicinity of both side edges of said inner member.

3. The disposable diaper of claim 1, further comprising tapes provided with large numbers of pores, said tapes being adhered to said inner member to cover said first and second cavities.

4. The disposable diaper of claim 1, wherein said first cavities are distributed substantially over the entire surface of said inner member.

5. The disposable diaper of claim 1, comprising further baby powder in locations on the rear side of said inner member.

6. The disposable diaper of claim 1, wherein said baby power is distributed in larger amounts in the vicinity along both side edges of said inner member.

7. The disposable diaper of claim 1, further comprising bags located in the vicinity of both side edges of said diaper, said bags having pores, and further pulverulent baby powder in said bags.

8. The disposable diaper of claim 7, wherein said bags are made of nonwoven fabric.

9. The disposable diaper of claim 7, wherein said bags are in the form of longitudinal cylinder type members having sealed end portions, said cylinder type members being arranged primarily along said side edges.

10. The disposable diaper of claim 9, further comprising longitudinal elastic members which are arranged in the vicinity of said side edges of said diaper for forming said elastic gathers, said bags being arranged along the inner sides of said elastic members.

11. The disposable diaper of claim 7, wherein said bags are arranged on the rear side of said inner member.

12. The disposable diaper of claim 1, further comprising at least two doubled Z-shaped portions each having a pair of oppositely bent parallel folds extending in the vicinity of said side edges of said inner member along the longitudinal direction of said side edges, so that said baby powder is received in a clearance defined in at least one bent portion provided in said double Z-shaped portions.

13. The disposable diaper of claim 1, further comprising longitudinal elastic members arranged between said inner member and said outer member to form said elastic gathers along portions close to both of said side edges of said inner and outer members, said elastic members being formed by flexible foam material, said elastic members forming bubbles, and further baby powder retained in said bubbles.

* * * * *

UNITED STATES PATENT AND TRADEMARK OFFICE
CERTIFICATE OF CORRECTION

PATENT NO. : 4,753,643

DATED : June 28, 1988

INVENTOR(S) : Kenzou Kassai

It is certified that error appears in the above-identified patent and that said Letters Patent is hereby corrected as shown below:

On the title page assignee should read

-- [73] Assignee: Aprica Kassai Kabushikikaisha, Osaka, Japan --.

Claim 1, line 17, replace "with" by --when--.

Signed and Sealed this

Eighth Day of November, 1988

Attest:

DONALD J. QUIGG

Attesting Officer

Commissioner of Patents and Trademarks